United States Patent [19]

Thomas et al.

[11] 3,969,149

[45] July 13, 1976

[54] THERMOELECTRIC MICROGENERATOR

[75] Inventors: Pierre Thomas, Briis-sous-Forges; Michel Alais, Orsay, both of France

[73] Assignee: Compagnie Industrielle des Telecommunications Cit-Alcatel, France

[22] Filed: Sept. 13, 1973

[21] Appl. No.: 396,706

[30] Foreign Application Priority Data

Sept. 13, 1972  France ............................. 72.32442

[52] U.S. Cl. ................................ 136/225; 136/208; 136/212
[51] Int. Cl.² .......................................... H01L 35/02
[58] Field of Search ........... 136/202, 205, 208, 211, 136/212, 224, 225; 62/3

[56] References Cited
UNITED STATES PATENTS 2,966,033  12/1960  Hughel ............................. 136/205 X
3,004,393  10/1961  Alsiny ................................. 136/225
3,617,390  11/1971  Erlangen ............................ 136/211

FOREIGN PATENTS OR APPLICATIONS 1,410,413  8/1965  France ................................ 136/211

*Primary Examiner*—Verlin R. Pendegrass
*Attorney, Agent, or Firm*—Craig & Antonelli

[57]  ABSTRACT

Very compact thermoelectric microgenerator providing a high output voltage (10 V) and having high efficiency, comprising a great number of thermocouples arranged in rows connected together so as to form a continuous conductor of deposited thin layers on a thin insulating support. The cold and hot sources are fitting provided with low walls parallel to one another and orthogonal to the rows of thermocouples. The even junctions of the thermocouples are placed in the vicinity of the low walls of the cold source and the odd junctions are placed in the vicinity of the low walls of the hot source. Application is to implanted medical appliances.

19 Claims, 8 Drawing Figures

THERMOELECTRIC MICROGENERATOR

The present invention relates to a thermoelectric microgenerator constituted by a great number of thermocouples connected up in series and arranged between an element acting as a cold source thermally coupled to the odd junctions of the thermocouples and an element acting as a hot source thermally coupled to the even junctions of the thermocouples.

Such microgenerators are used for example in implanted medical applicances for transforming heat energy coming from a heat source into electric energy.

A very small volume and sufficient efficiency are compulsory requisites for these microgenerators, this enabling a device having small dimensions to be obtained and the service life of the source to be increased.

Microgenerators having a small volume and high efficiency are already known, but they have the disadvantage of having a low output voltage (in the order of 1V).

These microgenerators comprise a certain number of thermocouples each constituted by a negative rod and a positive rod, all these rods being glued to one another and arranged between a hot wall and a cold wall, orthogonally to those walls. Using these known microgenerators, it was not possible to increase greatly the number of couples arranged in series without increasing the assembling difficulties to a prohibitive extent, as well as the price.

The invention aims at overcoming that disadvantage, enabling the producing of a microgenerator with a small volume, having excellent efficiency and supplying an output voltage in the order of a tenth of a volt.

The thermoelectric micorgenerator according to the invention which comprises a great number of thermocouples connected up in series and arranged between an element which acts as a cold source thermally coupled to the odd junctions of the thermocouples and an element which acts as a hot source thermally coupled to the even junctions of the thermocouples is characterized in that the thermocouples are arranged in rows connected together so as to form a continuous conductor deposited in the form of a thin layer on a thin support made of an electrically insulating substance which is a bad heat conductor and in that the elements acting as a cold source and a hot source are provided with grooves separated by low walls parallel to one another and orthogonal to the rows of thermocouples, the low walls of the cold source being situated in the vicinity of the odd junctions of the thermocouples and the low walls of the hot source being situated in the vicinity of the even junctions of the thermocouples.

The use of the thin layer technique enables a very great number of thermocouples having low impedance per surface unit to be obtained. The arrangement of the thermocouples in rows orthogonal to the low walls of the cold and hot sources enables an optimum transfer of heat towards the even junctions without affecting the odd junctions, as well as an optimum transfer of heat from the odd junctions towards the cold source.

Due to the structure of the microgenerator according to the invention, a great number of thermocouples whose electromotive powers are added so that the voltage obtained may reach 10 or so volts, this enabling that voltage to be used directly without reverting to the use of a voltage converter, may be connected together in series.

The following description with reference to the accompanying drawings will make it easier to understand how the invention may be implemented.

Figure 1:
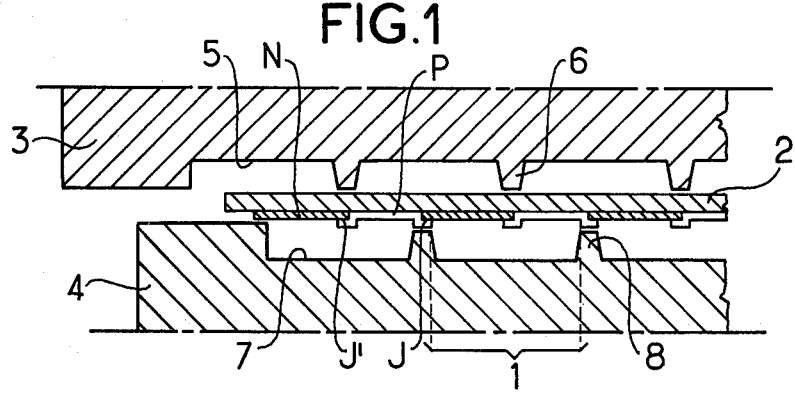
FIGS. 1 and 2 show a first embodiment of the microgenerator according to the invention.

The microgenerator such as shown in FIG. 1 comprises several thermocouples 1 in series, having equal lengths, constituted each by a negative element and a positive element having approximately equal lengths. These thermocouples 1 have been deposited in the form of thin layers on a plane thin support 2 made of an electrically insulating substance which is a bad heat conductor, for example, ethylene polyterephthalate.

The thin support is arranged between an element acting as a hot source 3 whose temperature is maintained in the order of 100°C. and an element acting as a cold source 4 whose temperature is maintained in the order of 40°C.

The hot source 3 comprises a plane face in which grooves 5 whose width is slightly less than the length of a thermocouple have been formed. These grooves 5 are separated by low walls 6 which are equidistant and parallel.

The cold source 4 also comprises a plane face in which grooves 7 have been formed, these grooves being separated by low walls 8 which are parallel and equidistant.

The low walls 6 and 8 have equal widths and are parallel to one another, the walls of the hot source overhanging the mid portion of the grooves 7 of the cold source.

The thin support 2 is placed parallel to the tops of the various low walls with the thermocouples on the side nearest the low walls 8 of the cold source.

All the even junctions J of the thermocouples, that is, the second and the fourth, etc., . . . from the left of the support 2 are placed in the immediate vicinity of the walls 8 of the cold source. Each wall 6 of the hot source is placed in the immediate vicinity of the support 2 so as to overhang an odd junction J'. The thin support and the hot and cold sources are rigidly fixed in relation to one another by fixing elements (not shown).

Figure 2:
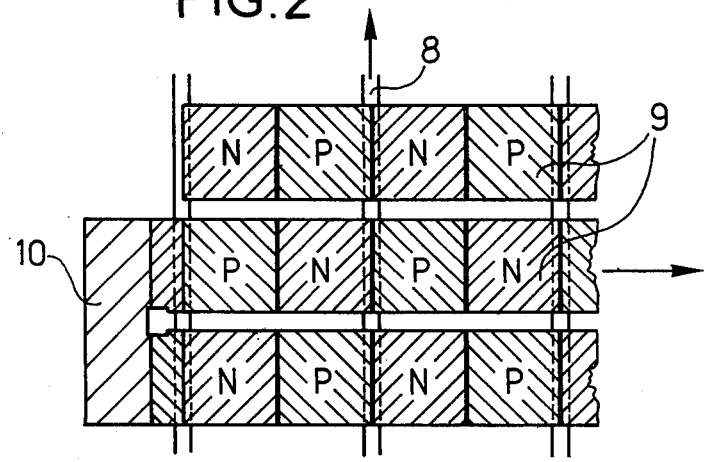

FIG. 2 shows a top view of the microgenerator according to the invention with the hot source and thin support removed.

The thermocouples 1 are arranged in parallel rows 9, each row being connected at one of its ends to the following row by a connecting bridge 10 so as to form thus a continuous conductor starting from a point of the support to end up at a terminal point.

The adjacent rows are spaced slightly apart from one another so as to prevent any electric or thermal contact between them.

These rows are orthogonal to the low walls 8 of the cold source and also to the low walls of the hot source (not shown on that figure).

Looking along the continuous conductor formed by the thermocouples in series, a negative element followed by a positive element will be alternately found and each negative element of a row is therefore surrounded by four positive elements, two belonging to the same row and two belonging to the adjacent rows.

Figure 3:
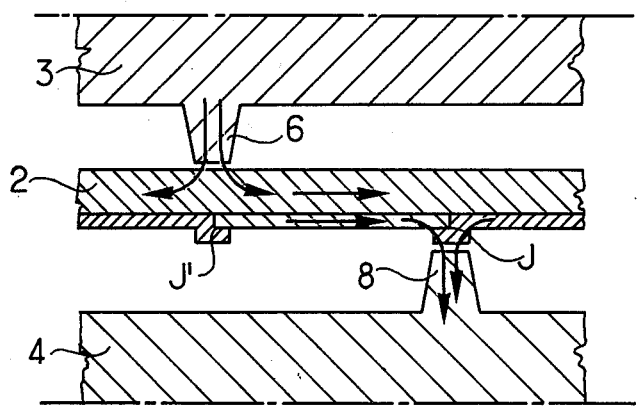
FIG. 3 is an explanatory diagram of the operation of a thermocouple.

FIG. 3 shows diagrammatically the path of the heat flux. The heat coming from the hot source passes through the low wall 6 and is communicated to a thin strip of the thin support 2 situated adjacent to that low wall.

The junction J' is heated and the heat is propagated along the thermoelements up to the low walls 8 of the cold source.

Figure 4:
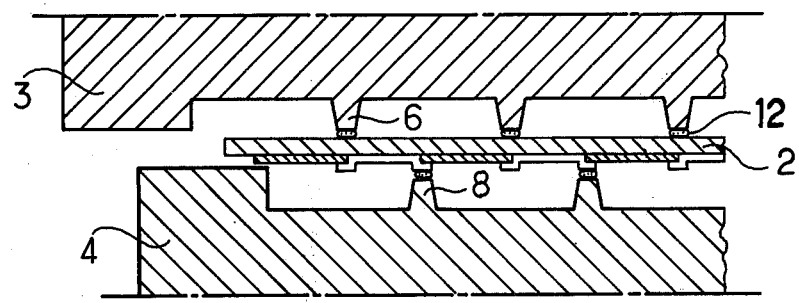
FIG. 4 shows a first variant of the microgenerator according to the invention.

To promote thermal coupling between the low walls 6 and 8 and the junctions J and J', the end of the low walls 8 of the cold source are stuck with the even junctions J arranged adjacent to these low walls and the end of the walls of the hot source are stuck with the thin support 2 (see FIG. 4). Due to the presence of these drops of glue 12, the heat is propagated more easily between the low walls and the junctions of the thermocouples and the microgenerator assembly. Moreover, the solidity of the assembly is thus improved.

Figure 5:
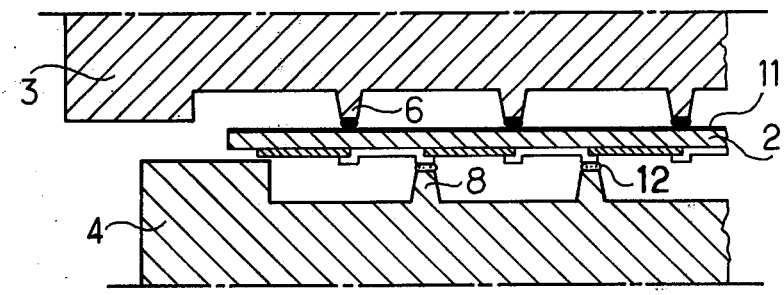
FIG. 5 shows a second variant of the microgenerator according to the invention.

According to an improvement, to the invention, shown in FIG. 5, to improve the solidity of the assembly, a layer of metal 11 is arranged on the thin support 2 on the opposite side to that of the thermocouples and the low walls 6, of the hot source are welded with that layer 11.

The walls of the cold source are stuck to the even junctions J of the thermocouples.

Figure 6:
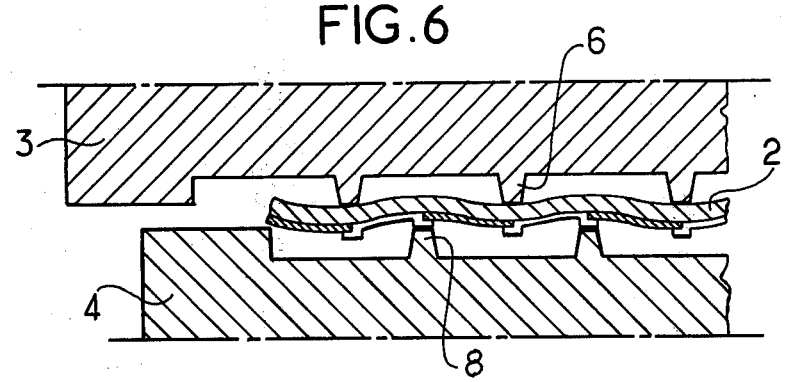
FIG. 6 shows a third variant of the microgenerator according to the invention.

FIG. 6 shows a variant of embodiment of the microgenerator according to the invention in which the low walls 8 of the cold source and the low walls 6 of the hot source have been brought closer together so as to come into contact with the thin support 2 and to impart to it a slightly corrugated shape thus promoting thermal contact between the low walls and the junctions. In that embodiment, the low walls 8 of the cold source have been coated with a thin layer of electric insulant, glue, for example.

Figure 7:
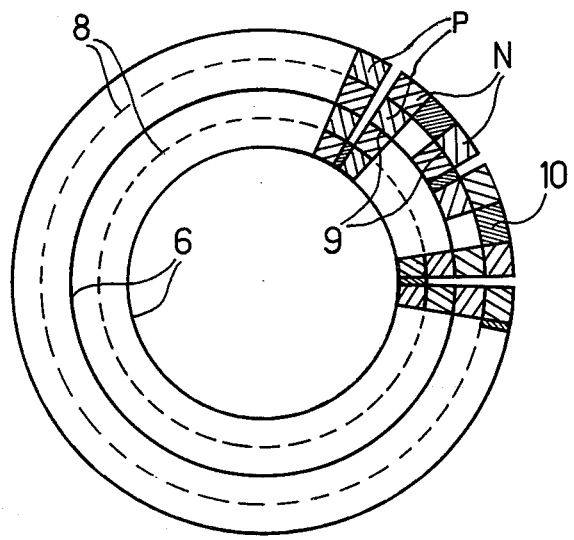
FIG. 7 shows a second embodiment of the microgenerator according to the invention.

FIG. 7 shows a second embodiment in which the low walls of the cold and hot sources are no longer rectilinear as in the embodiment shown in FIGS. 1 and 2 but have ths shape of concentric circles. The thermocouples are arranged in rows 9 orthogonal to the walls 6 and 8, that is, in radii of the concentric circles.

The low walls of the hot source overhang, as in the preceding embodiment, the mid portion of the grooves in the cold source.

Figure 8:
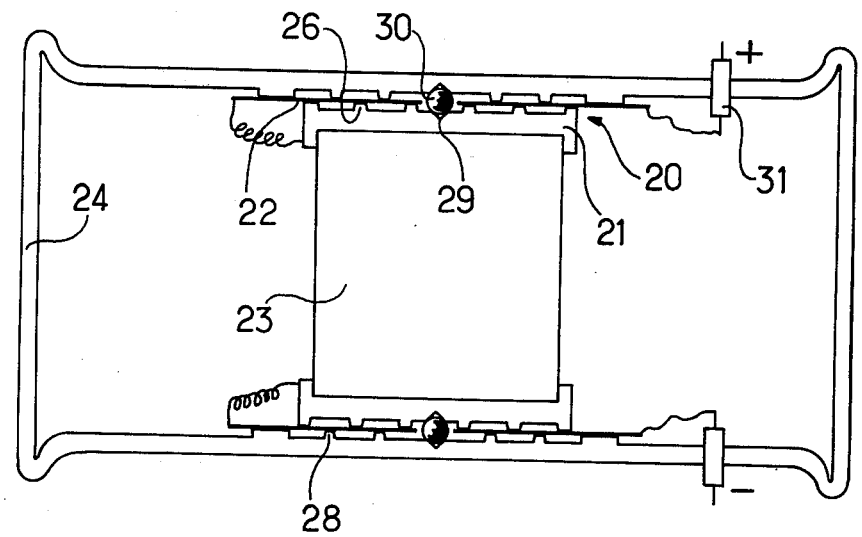
FIG. 8 shows a microgenerator according to the invention, capable of being fitted to a heart stimulator.

FIG. 8 shows diagrammatically a microgenerator in the invention which may be fitted to a heart stimulator.

The microgenerator comprises a cylindrical casing 24 having a vertical axis inside which is arranged a heat source 23 in the form of a straight cylinder having a vertical axis.

The source 23 is provided at both its ends with a metallic cap 21 in which have been formed grooves separated by low concentric walls 26.

The casing 24 is provided at its lower part and at its upper part with low concentric walls 28 having the same axis as those of the hot source.

This heart stimulator uses two microgenerators 20 similar to that shown in FIG. 7. Each microgenerator comprises a thin support 22 on which thermocouples are deposited as shown in FIG. 7.

To ensure good stability of the assembly, the low walls 28 of the cold source are stuck with the even junctions and the low walls 26 of the hot source are stuck with the thin supports 22. To improve that stability and to ensure good resistance to shocks, recesses 29 have been provided in the hot and cold sources at the center of each group of low circular walls in which a ball 30 made of an insulant, for example a ceramic substance, has been accommodated. The two microgenerators 20 are connected up in series and are each joined to an electric output terminal 31. To ensure better use of the heat, the casing is filled with a heat insulant.

The casing is at a temperature in the order of that of the human body that is, 40°C., and the heat source is a small plutonium battery having a power of 100 milliwatts, whose temperature is in the order of 100°C.

Using positive and negative bismuth telluride thermocouples deposited in thin layers, the voltage reached at the output terminals of the microgenerator is in the order of 12 volts, this enabling the use of that voltage directly without going through a voltage converter.

Numerous variants of the microgenerators described are possible, more particularly, the thin support provided with the thermocouples could be turned over so that the thermocouples face the low walls of the hot source and the thin support face the low walls of the cold source.

Several balls made of ceramic substances jammed between the two sources to act as a stop and to increase the resistance to shocks could also be used.

Although the microgenerator which has just been described may appear to afford the greatest advantages for implementing the invention, it will be understood that various modifications may be made thereto without going beyond the scope of the invention, it being possible to replace some of its elements by other elements capable of ensuring the same technical function or an equivalent technical function therein.

More particularly, it would be possible to use a hot source having a face fitted with low walls which is not plane (cylindrical, for example) connected with a thin support having the same curve and to a cold source provided with low walls bearing on the thin support.

What is claimed is:

1. A thermoelectric microgenerator comprising a plurality of thermocouples connected in series, said thermocouples being formed by rows of alternately arranged positive and negative elements connected together to form a continuous conductor, said positve and negative elements being thin layers disposed on one side of a thin support, said thin support being an electrical insulating material and a poor heat conductor, a cold source having spaced projections disposed in thermal contact with alternate junctions of said thermocouples, and a hot source having spaced projections disposed in thermal contact with other alternate junctions of said thermocouples not in thermal contact with said projections of said cold source.

2. A thermoelectric microgenerator according to claim 1, characterized in that the rows of thermocouples form a network of segments of straight lines parallel to one another and orthogonal to the porjections of the cold and hot sources, said projections also being arranged in networks of segments of parallel straight lines.

3. A thermoelectric microgenerator according to claim 1, characterized in that said projections of the cold source and those of the hot source are arranged in networks of concentric circles and in that the rows of thermocouples are arranged in radii of those circles.

4. A thermoelectric microgenerator according to claim 1, characterized in that the projections of the hot source are secured to the thin support and in that the projections of the cold source are secured to said alternate junctions of the thermocouples.

5. A thermoelectric microgenerator according to claim 1, characterized in that the projections of the hot source are welded to a metal layer deposited on the thin support on the side opposite to that of the thermocouples and in that the projections of the cold source are bonded to said alternate junctions of the thermocouples.

6. A thermoelectric microgenerator according to claim 1, characterized in that the projections of the cold source are covered with a thermal insulant and bear strongly against said alternate junctions of the thermocouples and in that the projections of the hot source bear strongly against the thin support.

7. A thermoelectric microgenerator according to claim 1, characterized in that the hot and cold sources are provided with at least one recess oppositely disposed to one another and at least one ball made of a ceramic substance disposed in said recess for ensuring the positioning of the projections of the hot source in relation to those of the cold source.

8. A thermoelectric microgenerator as defined in claim 1 wherein said support and said hot and cold sources are planar elements, the projections of said hot and cold sources being directed toward said support with said support being disposed therebetween.

9. A thermoelectric microgenerator as defined in claim 8 wherein a metal layer covers the side of said support facing said hot source.

10. A thermoelectric microgenerator as defined in claim 9, characterized in that the projections of the hot source are secured to the thin support and in that the projections of the cold source are secured to said alternate junctions of the thermocouples.

11. A thermoelectric microgenerator according to claim 10, characterized in that the rows of thermocouples form a network of segments of straight lines parallel to one another and orthogonal to the projections of the cold and hot sources, said projections also being arranged in networks of segments of parallel straight lines.

12. A thermoelectric microgenerator according to claim 10, characterized in that said projections of the cold source and those of the hot source are arranged in networks of concentric circles and in that the rows of thermocouples are arranged in radii of those circles.

13. A thermoelectric microgenerator according to claim 1, wherein each of said cold and hot sources respectively include a planar surface is facing relationship to said thin support, said planar surface including a plurality of grooves being separated by ridges projecting from said planar surface toward said thin support, said ridges forming said projections.

14. A thermoelectric microgenerator according to claim 13, wherein each of said ridges is formed with walls of low height.

15. A thermoelectric microgenerator according to claim 13, wherein said ridges between the grooves of one planar surface are in facing relationship with the mid portion of the grooves of the respective oppositely disposed planar surface.

16. A thermoelectric microgenerator according to claim 1, wherein said projections include ridges formed with walls of low height.

17. A thermoelectric microgenerator according to claim 1, wherein said thin support is a thin planar member, said thin layers of said positive and negative elements being disposed on one planar surface of said member.

18. A thermoelectric microgenerator according to claim 1, wherein said projections of said cold source are disposed against the side of said thin support opposite said thin layers of said positive and negative elements.

19. A thermoelectric microgenerator according to claim 1, wherein said projections of each of said hot and cold sources contact respective opposite sides of said thin support to impart a corrugated shape to said thin support.

* * * * *